United States Patent [19]

Leser

[11] Patent Number: 5,258,611
[45] Date of Patent: Nov. 2, 1993

[54] LIGHT EMISSION OR ABSORPTION DEVICE FOR THE CONTACTLESS INSPECTION OF ARTICLES HAVING A PLURALITY OF LIGHT SOURCES AND AN ELONGATE LIGHT GUIDE

[75] Inventor: Jacques Leser, Lunel, France

[73] Assignee: Verreries du Languedoc, Vergeze, France

[21] Appl. No.: 944,467

[22] Filed: Sep. 11, 1992

[30] Foreign Application Priority Data

Sep. 11, 1991 [FR] France ............................ 91 11227

[51] Int. Cl.⁵ ............................................. G01N 9/04
[52] U.S. Cl. .................... 250/223 B; 356/240
[58] Field of Search ............... 250/223 B, 571, 572; 356/240, 239, 428

[56] References Cited

U.S. PATENT DOCUMENTS 4,171,481 10/1979 Mima .
4,885,461 12/1989 Mattila et al. ............... 356/240
4,902,137 2/1990 Krieg et al. ............... 356/240

FOREIGN PATENT DOCUMENTS 0177004 4/1986 European Pat. Off. .
0218865 4/1987 European Pat. Off. .

*Primary Examiner*—David C. Nelms
*Assistant Examiner*—Que T. Le
*Attorney, Agent, or Firm*—Helfgott & Karas

[57] ABSTRACT

Light emission or absorption device used in combination with at least one optical detection device including a linear array of reception photodiodes having a view of articles for the contactless inspection thereof, in particular of glass articles at high temperature, comprises a casing equipped with an opening in the form of an elongate slot flanked by two parallel plates forming a light guide. The casing contains a semi-reflecting mirror, an illumination device situated behind the mirror with respect to the slot, and an alignment of a plurality of individual lamps placed so that the light emitted by the lamps is reflected by the mirror in the direction of the slot. It is thus possible to carry out an accurate alignment adjustment by means of the aligned lamps before carrying out the inspection in bright field, by switching on the tubes, or in dark field by switching them off.

9 Claims, 4 Drawing Sheets

LIGHT EMISSION OR ABSORPTION DEVICE FOR THE CONTACTLESS INSPECTION OF ARTICLES HAVING A PLURALITY OF LIGHT SOURCES AND AN ELONGATE LIGHT GUIDE

BACKGROUND OF INVENTION

The present invention relates to a light emission or absorption device which is intended to be associated with at least one optical detection device including a linear array of reception photodiodes for contactless inspection of articles, in particular of glass articles or containers at high temperature.

The mass production of articles at high rate requires the organization of quality control procedures which are effective and do not lead to excessive costs. Thus, in particular for the manufacture of molded articles which leave the mold at high temperature, optical inspection devices are usually used.

French Patent Application 84/15,117 relates especially to a method and a device permitting such an inspection of glass articles manufactured by injection-blow molding. The inspection is carried out by illuminating the containers and detecting the light traversing the container which moves perpendicularly to the illumination device, by means of a linear measurement array equipped with a plurality of photodiodes. This document provides, by way of light source, a fluorescent tube whose longitudinal axis is parallel to that of the measurement array.

In the same manner, U.S. Pat. No. 4,476,533 teaches an inspection device using transmission of light emitted in the direction of a linaer array of photodiodes. British Patent 2,135,452 provides for the inspection of translucent containers by subjecting these to a rotation in front of a linear ray which is directed intermittently onto the container in a direction substantially parallel to its rotation axis. Mention may also be made of French Patent 2,475,424 and of European Patent 60,160 which both use optical systems, whether for the identification of containers or for the inspection of sheet glass.

In all these documents the light sources used are either not specified or are simply mentioned in outline.

However, it has been observed in practice that the structure of the illumination device used in the methods and devices for contactless inspection of articles was of considerable significance for the reliability of the inspection. This also applies in particular to the case in which the inspection is brought about by means of an optical detection device equipped with a linear array of reception photodiodes which are arranged in an alignment orthogonal to the movement of the articles to be inspected.

SUMMARY OF THE INVENTION

An object of the present invention is therefore to provide a device which can be associated with such an optical detector so as to improve the quality and the reliability of the inspection obtained.

Another object of the invention is the production of a device which can be used in the case of the shape recognition or analysis or inspection of articles by reflection or by transmission of light without any modification.

Finally, yet another object of the invention is to facilitate the initial position adjustment of the various elements of an installation for inspecting articles using an optical detector equipped with a linear array of reception photodiodes.

The light emission or absorption device according to the invention is intended to be associated with at least one optical detection device including a linear array of reception photodiodes with a view to the contactless inspection of articles, in particular of glass articles at high temperature. According to the invention, the device comprises a casing equipped with an opening in the form of an elongate slot flanked by two parallel plates forming a light guide. The casing includes a semireflecting mirror, an illumination means situated behind the mirror with respect to the slot and a plurality of individual lamps arranged in alignment, the lamps being placed so that the light emitted by substantially point sources, which the individual lamps constitute, is reflected by the mirror in the direction of the elongate slot.

Thus it is possible to make a very accurate position adjustment by using the aligned individual lamps and by checking their alignment with respect to that of the linear array of reception photodiodes.

Moreover, the device can be used as a light emitter by employing the illumination means whose light transverses the semi-reflecting mirror and is guided by two parallel plates in the direction of the article to be inspected and then towards an optical detection camera or device equipped with the linear array of reception photodiodes.

It is also possible, in another embodiment of a shape analysis or inspection installation, to use another light source whose light is reflected by the article to be inspected in the direction of the optical detection device. The device of the invention then acts as a light absorption device permitting the production of a dark field along the axis of the linear array of reception photodiodes behind the article to be inspected by virtue of the light guide formed by the two parallel plates.

The illumination means advantageously comprises at least one fluorescent tube placed in parallel with the elongate slot whose length is at least equal to that of the slot. In a preferred embodiment, the illumination means comprises two fluorescent tubes placed side by side so as to provide a luminous area, without interruption, as seen from the elongate slot. In order to obtain this result, it suffices, for example, to overlap the two parallel fluorescent tubes slightly.

The width of the slot is preferably chosen to be as small as possible with respect to the extent of the luminous area created by the illumination means. Such a fine slot, combined with a large illumination surface inside the casing of the device, allows effective scanning of the article to be controlled, in front of the optical detection device, to be obtained.

In order to prevent the penetration of dust existing in the environment of the inspection installation, the casing is preferably pressurized by a compressed gas, for example compressed air, and comprises for this purpose an orifice for supply with pressurized gas, the gas continuously escaping via the open slot.

The semi-reflecting mirror is advantageously of elongate shape and of length at least equal to that of the slot. It is placed at 45° with respect to the slot so as to permit both the transmission of the light coming from the illumination means by transmission and the reflection of the light coming from the alignment of the individual lamps in the direction of the elongate slot.

The device furthermore comprises means for switching on the individual lamps independently of the switching-on of the illumination means.

The invention will be better understood by studying a particular embodiment described by way of entirely non-limiting example and illustrated by the attached drawings.

DETAILED DESCRIPTION OF THE PREFERRED EMBODIMENTS

Figure 1:
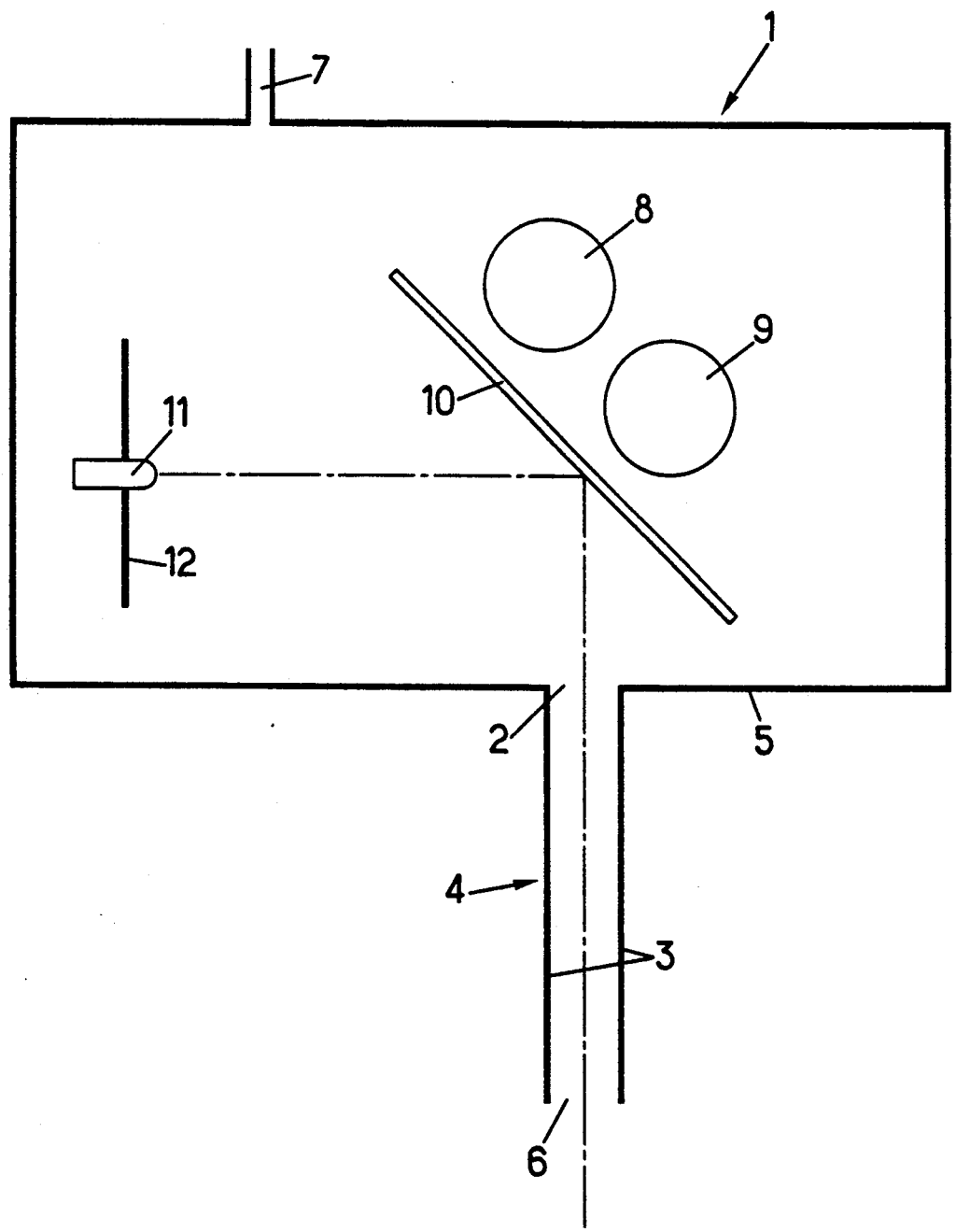
FIG. 1 is a diagrammatic plan view of a device according to the invention.
Figure 2:
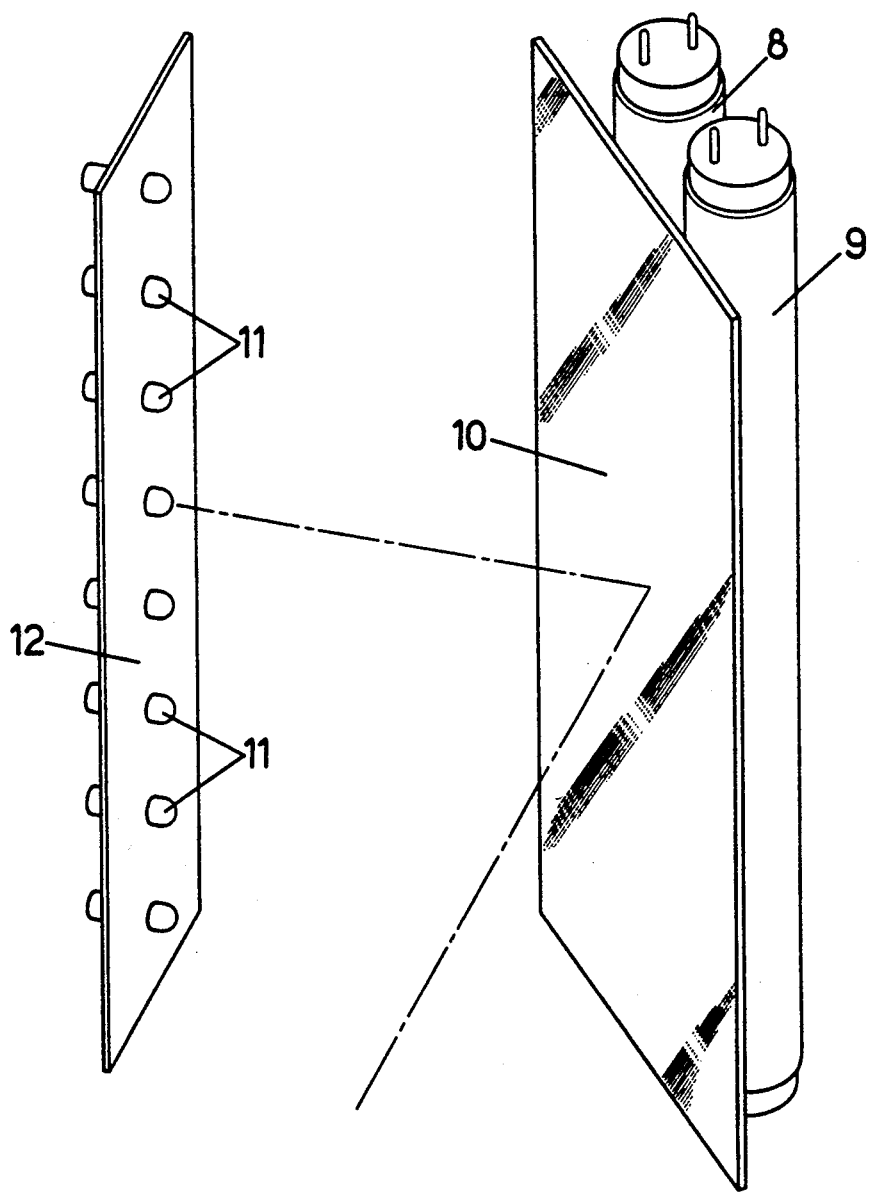
FIG. 2 is an exploded perspective view of the principal components of the device of the invention, as they are mounted inside the casing, the latter not having been shown.

As illustrated in FIGS. 1 and 2, the device of the present invention comprises a casing 1 equipped with an opening in the form of an elongate slot 2 which is flanked by two parallel plates 3 forming a light guide 4. The plates 3 extend perpendicularly to the front face 5 of the casing 1 and they define, in the vicinity of their free end, a further open slot 6 parallel to the slot 2. The casing is completely closed apart from the slot 2 and an orifice 7 provided for permitting the supply of the casing with pressurized compressed air, this compressed air escaping via the slot 2 and then between the plates 3 via the slot 6, and thus preventing any dust from penetrating inside the casing 1.

Inside the casing 1 are mounted the principal components of the device. These comprise, as may be seen in FIGS. 1 and 2, an illumination means constituted by two fluorescent tubes 8 and 9 mounted in parallel with the slot 2. The fluorescent tubes 8 and 9 are slightly longer than that of the slot 2 so as to illuminate the latter completely over its entire length. A semi-reflecting mirror 10 is mounted in parallel with the tubes 8 and 9, making an angle of 45° with the plane of the slot 2, that is to say with the front face 5 of the casing 1.

A plurality of individual lamps 11 constituted by light-emitting diodes are mounted in alignment with each other on a plate 12 fixed in the casing by any suitable means which are not shown. The plate 12 supporting the individual lamps 11 is mounted in the casing at 45° with respect to the mirror 10. As may be seen in FIGS. 1 and 2, the light emitted by the substantially point sources, which the individual lamps 11 constitute, is reflected by the reflecting face of the mirror 10 so as to penetrate perpendicularly into the slot 2 and the light guide 4. The light path is represented in FIGS. 1 and 2 by a dot-dash line.

As for the light emitted by the two fluorescent tubes 8 and 9, this traverses the mirror 10 and constitutes a wide luminous area which is partly seen by the slot 2 and from outside by the light guide 4.

In order for this luminous area to be without interruption, the fluorescent tubes 8 and 9 are arranged so that their outlines, such as seen in FIG. 1, overlap slightly. A part of the luminous tube 8 is thus behind the fluorescent tube 9 if the combination is seen from the slot 2. As may be noted from the figures, the tubes 8 and 9 are arranged behind the semi-reflecting mirror 10 with respect to the slot 2, their axes defining a plane parallel to that of the mirror 10.

Figure 3:
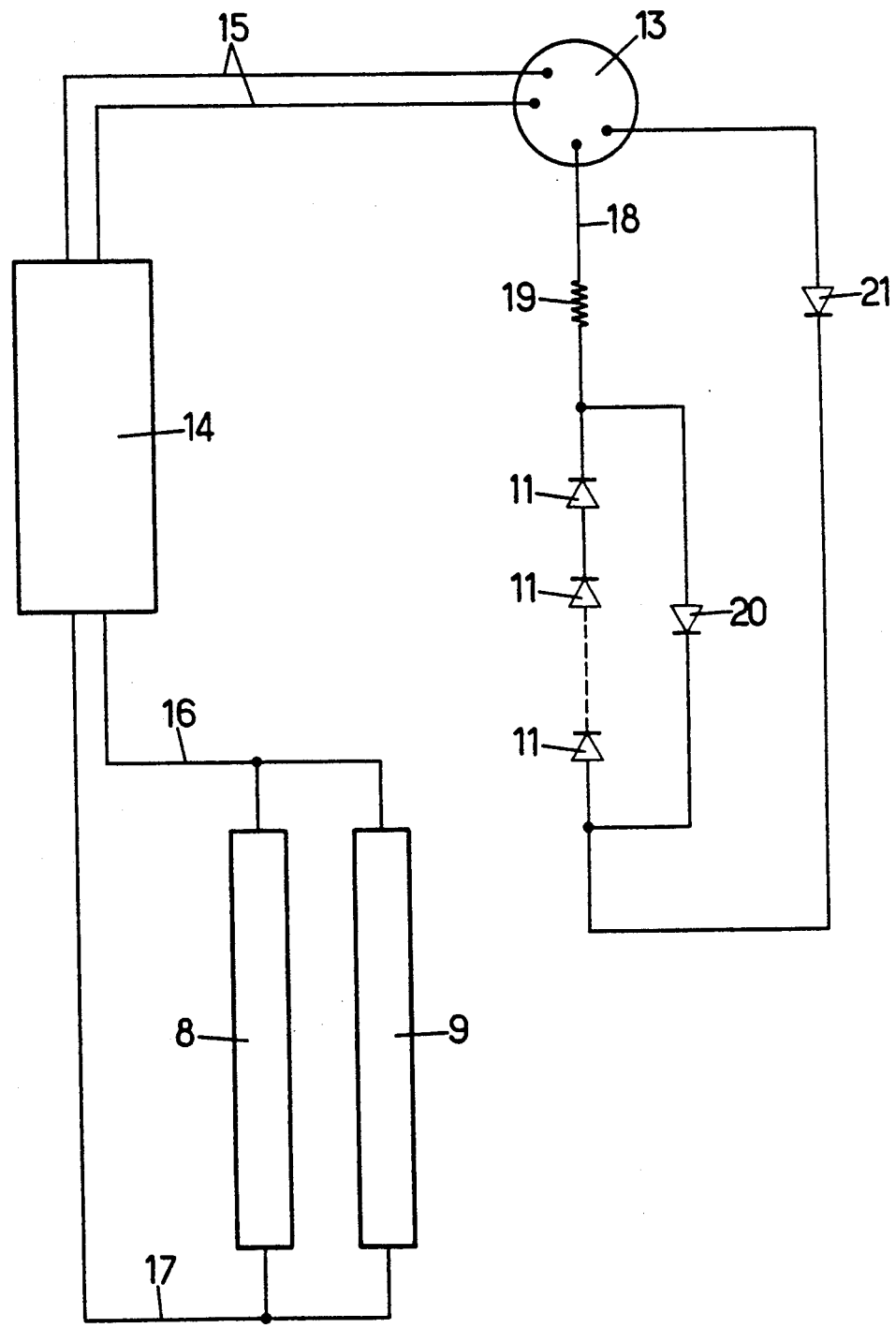
FIG. 3 illustrates diagrammatically the electrical supply of the device.

Reference will now be made to FIG. 3, in which the electrical supply of the whole device is shown.

A connector 13 situated behind the casing 1, and not shown in FIG. 1, permits the supply of a voltage-frequency power converter 14 via connection lines 15. The converter 14 is connected via the connection lines 16 and 17 to the two terminals of the fluorescent tubes 8 and 9. The connector 13 is also connected via a connection line 18 to a resistor 19 permitting the electrical current to be limited, the resistor 19 being connected to the terminals of various series-mounted light-emitting diodes 11.

A diode 20, mounted with reverse polarity across the terminals of the set of light-emitting diodes 11 enables any destruction, in the event of reverse-polarity voltage, to be avoided. An additional diode 21 is also series mounted between the connector 13 and the set of diodes 11 so as to prevent possible parasitic voltages.

Figure 4:
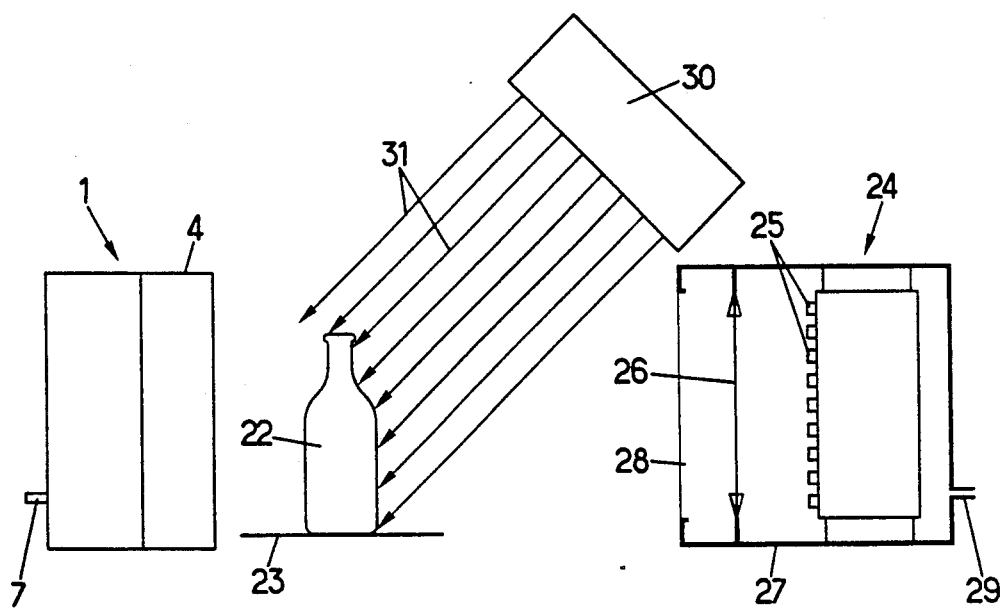
FIG. 4 illustrates diagrammatically a first mode of use of a device according to the invention.
Figure 5:
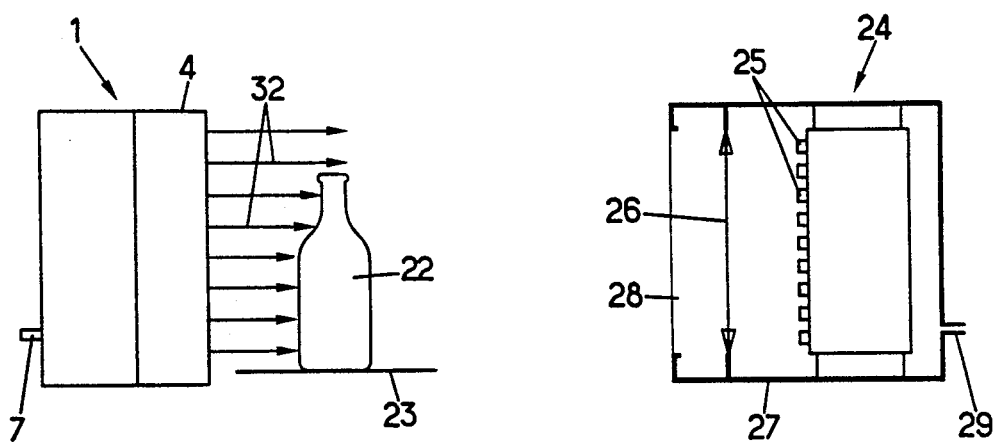
FIG. 5 illustrates diagrammatically a second mode of use of the device of the invention.

Reference will now be made to FIGS. 4 and 5 in order to understand the mode of use of the device of the invention.

In FIG. 4, use is made of the device of the invention, in which the casing 1 and the light guide 4 may be distinguished, as a light absorber. The purpose of the installation is the shape recognition and analysis or inspection of glass containers 22 which move on a belt conveyor 23 perpendicularly to the inspection installation. In addition, the latter comprises the device of the invention, an optical detection device 24 including a linear array of reception photodiodes 25, which array is placed at the focus of an optical focusing device 26. The whole optical detection device is arranged inside a casing 27 equipped with an open slot 28 which is of elongate shape and disposed in parallel with the array of photodiodes 25, which array is itself parallel to the elongate slot of the casing 1 of the device of the invention. The casing 27 of the optical detection device is also subjected to the pressure of compressed air supplied via the orifice 29 in order to prevent any penetration of dust onto the optical component 26.

An additional illumination source 30 is placed above the optical detection device 24 so as to emit a light beam 31 in the direction of the container 22 to be analyzed. Possible defects or modifications of the surface state of the container 22 then generate, by reflection, a light signal in the direction of the optical detection device 24.

The device of the invention permits an accurate adjustment of the alignment of the camera of the optical device 24 with respect to the whole installation. In order to perform this accurate alignment, a coarse adjustment is first made by switching on the fluorescent tubes 8 and 9 situated inside the casing 1. Next the fluorescent tubes are switched off and the light-emitting diodes 11 are switched on. The optical detection device 24 is then adjusted so as to obtain an accurate alignment of the light-emitting lamps 11 of the device of the invention, which are situated in the casing 1, with the array of reception photodiodes 25. If necessary the casing 1 is rotated in order to obtain the accurate alignment. The light-emitting lamps 11 are then switched off without switching on the fluorescent tubes 8 and 9. The light guide 4, constituted by the parallel plates 3 in association with the casing 1, then produces a light absorption device which permits a narrow dark field to be defined which is precisely aligned with the array of photodiodes 25 and on which the defects giving rise to a deflection of the light coming from the additional illumination source 30 may be observed accurately.

In the mode of operation illustrated in FIG. 5, in which the same designations are used for the same components, it may be seen that the installation does not include an additional light source as was the case in the embodiment of FIG. 4. The adjustment of the alignment is brought about as before. After this operation, the fluorescent tubes 8 and 9 are switched on and the device of the invention 1 is used as an illumination device capable of transmitting a narrow light beam 32 in the direction of the container 22. The defects or the shape fluctuations are then detected by particular reflection of the light which reaches the reception photodiodes 25.

By virtue of the invention, an extremely simple and practical device is obtained, permitting the reliability of the system for shape recognition and analysis or inspection of moving articles, and in particular of glass articles at high temperature, to be facilitated and improved. The inspection of the articles can be carried out by transparency, for example when they are made of glass, or by reflection. In other applications, it is only necessary to obtain the profile of the article. The device of the invention permits the detection to be facilitated every time.

What is claimed is:

1. Light emission or absorption device in combination with at least one optical detection device including a linear array of reception photodiodes arranged to view articles for a contactless inspection thereof, the light emission or absorption device comprising a casing including an opening in the form of an elongate slot enclosed by two parallel plates forming a light guide, a semireflecting mirror, an illumination means situated behind the mirror with respect to the slot, and a plurality of individual lamps arranged in alignment with each other and constituting substantially point light sources; said mirror, said illumination means and said lamps being contained in said casing, said individual lamps being placed in said casing so that the light emitted by the substantially point light sources is reflected by the mirror in the direction of the slot.

2. Combination according to claim 1, wherein the illumination means comprises at least one fluorescent tube placed in parallel with the slot and having a length which is at least equal to that of the slot.

3. Combination according to claim 2, wherein the illumination means comprises two fluorescent tubes placed side by side so as to provide a luminous area without interruption as seen from the slot.

4. Combination according to claim 3, wherein the width of the slot is small with respect to the luminous area provided by the illumination means.

5. Combination according to claim 1 wherein the casing comprises an orifice for supplying the casing with pressurized gas, the gas continuously escaping via the slot in order to prevent penetration of the dust into the casing.

6. Combination according to claim 1 wherein the semi-reflecting mirror is of elongate shape and of the length at least equal to that of the slot.

7. Combination according to claim 1 wherein the semi-reflecting mirror is positioned at 45° with respect to the slot.

8. Combination according to the claim 1, and further comprising means for switching on the individual lamps independently of switching-on of the illumination means.

9. The combination according to claim 1, wherein said articles are glass articles at high temperature.

* * * * *